(12) United States Patent
Bono

(10) Patent No.: US 6,230,703 B1
(45) Date of Patent: May 15, 2001

(54) AEROSOL INHALATION DEVICE PROVIDING IMPROVED AEROSOL DELIVERY

(76) Inventor: Michael Bono, 882 Black Rd., Collegeville, PA (US) 19426

( * ) Notice: Subject to any disclaimer, the term of this patent is extended or adjusted under 35 U.S.C. 154(b) by 0 days.

(21) Appl. No.: 09/324,275

(22) Filed: Jun. 2, 1999

(51) Int. Cl.⁷ .................................................. A61M 11/00
(52) U.S. Cl. ................... 128/200.14; 128/200.18
(58) Field of Search ........................ 128/200.14, 200.16, 128/200.18, 200.19, 203.15

(56) References Cited

U.S. PATENT DOCUMENTS

| | | | |
|---|---|---|---|
| Re. 31,785 | * 1/1985 | Netteland | 128/204.26 |
| 1,244,661 | * 10/1917 | Teter | 128/205.24 |
| 4,116,387 | * 9/1978 | Kremer, Jr. et al. | 128/200.18 |
| 4,674,491 | * 6/1987 | Brugger et al. | 128/200.18 |
| 4,823,784 | 4/1989 | Bordoni et al. | 128/200.14 |
| 5,165,392 | * 11/1992 | Small, Jr. | 128/200.18 |
| 5,235,969 | * 8/1993 | Bellm | 128/200.18 |
| 5,241,954 | * 9/1993 | Glenn | 128/200.18 |
| 5,355,872 | * 10/1994 | Riggs et al. | 128/203.15 |
| 5,458,135 | * 10/1995 | Patton et al. | 128/200.18 |
| 5,603,314 | 2/1997 | Bono | 128/200.21 |
| 5,611,332 | 3/1997 | Bono | 128/200.18 |
| 5,630,409 | 5/1997 | Bono et al. | 128/200.18 |
| 5,887,586 | 3/1999 | Dahlback et al. | 128/204.22 |
| 5,894,964 | 4/1999 | Barnes et al. | 222/402.1 |
| 5,899,201 | 5/1999 | Schultz et al. | 128/200.23 |

* cited by examiner

*Primary Examiner*—Aaron J. Lewis
(74) *Attorney, Agent, or Firm*—Duane, Morris & Heckscher, LLP

(57) ABSTRACT

Improved aerosol inhalation devices are provided. The devices include an aerosol source for generating an aerosol; a first conduit, having a proximal end, the first conduit providing passage of the aerosol to the patient; a first chamber at the proximal end of the first conduit, adjacent to the aerosol source; a second conduit providing passage of gaseous medium from the patient; a second chamber; and a first valve disposed between the first chamber and the second chamber. The first valve remains closed during exhalation by the patient and opens at least partially during inhalation. The device also includes a second valve disposed between the second conduit and the second chamber, which remains closed during inhalation by the patient and opens at least partially during exhalation by said patient. The gaseous medium exhaled by the patient can optionally contain material of which the aerosol is formed, such as liquid droplets. The invention also provides methods for making the devices, and for using the devices to deliver therapeutic and diagnostic material in aerosol form to a patient.

27 Claims, 3 Drawing Sheets

AEROSOL INHALATION DEVICE PROVIDING IMPROVED AEROSOL DELIVERY

FIELD OF THE INVENTION

This invention relates to methods of producing aerosols for delivery to patients, and in particular, to methods and devices for reducing the loss of aerosol therapeutic and diagnostic material within aerosol inhalation equipment.

BACKGROUND OF THE INVENTION

Aerosol inhalation devices are used in medical facilities in diagnostic and therapeutic procedures. Such devices are especially useful in pulmonary therapy for pneumonia and for introducing agents such as radioactive vapors for diagnosing diseases. With the advent of new treatments such as gene therapies, there are likely to be increased needs for aerosol inhalation devices that can effectively deliver medicaments to patients.

Aerosol inhalation devices include aerosol-generating equipment, and a means for delivering aerosol to a patient. An example of equipment for generating an aerosol from quid generally is a nebulizer, a device that mixes pressurized air or oxygen with diagnostic or therapeutic materials to create an aerosol. During generation of a liquid aerosol, a liquid to be aerosolized is placed in a reservoir in the nebulizer. Gas such as pressurized air or oxygen enters the nebulizer and acts to draw the liquid up through a delivery tube to an aerosol exit orifice, similar to the operation of a jet pump. At the aerosol exit orifice, the liquid is atomized into a mist referred to as an "aerosol". In some devices, larger drops that are produced in the mist impinge on baffles above the aerosol exit orifice where they drain back into the reservoir of the nebulizer. Smaller drops are entrained by the gas and are carried through the delivery system to the patient's lungs. Nebulizers are disclosed in U.S. Pat. Nos. 4,823,784 and 5,630,409, the disclosures of which are hereby incorporated herein by reference in their entirety.

Since most aerosol inhalation devices are currently made for a single use and are thereafter disposed, any medication or diagnostic material remaining in a device becomes waste. In addition, the greater the volume of the device, the lower the efficiency of delivery of aerosol to a patient, and the greater the air or oxygen pressure that can be required to deliver the aerosol. Valves within the path of aerosol delivery can further decrease efficiency by interrupting the flow of aerosol, affecting the pressure of the gas entering the device, and/or entrapping aerosol particles.

There have been few improvements directly related to efficiency of delivery and reduction of waste. In view of these and other recognized deficiencies of current devices, a need remains for improved aerosol delivery devices.

SUMMARY OF THE INVENTION

This invention provides aerosol inhalation devices for delivering aerosols to patients. In preferred embodiments, the devices include a means for generating an aerosol, a pair of conduits for providing passage of the aerosol to the patient and exhalate from the patient, and one-way valves to control the flow of aerosol and exhalate during administration of aerosol to a patient. The devices of the present invention employ an improved system of valves that eliminates the need for complex valve mechanisms having interstices in which therapeutic materials can become entrapped. The valves are placed so that they provide minimal obstruction of the flow of aerosol.

In one aspect, the invention provides an aerosol inhalation device for delivering an aerosol to a patient. The device includes an aerosol source for generating an aerosol; a first conduit, having a proximal end, the first conduit providing passage of the aerosol to the patient; a first chamber at the proximal end of the first conduit, adjacent to the aerosol source; a second conduit providing passage of gaseous medium from the patient; a second chamber; and a first valve disposed between the first chamber and the second chamber. The first valve remains closed during exhalation by the patient and opens at least partially during inhalation. The device also includes a second valve disposed between the second conduit and the second chamber, which remains closed during inhalation by the patient and opens at least partially during exhalation by the patient. The gaseous medium exhaled by the patient can optionally contain material of which the aerosol is formed, such as liquid droplets. The device can optionally include an exhaust port, located proximally from the second conduit. The exhaust port can be adjacent to the second chamber such as, for example, above the second chamber. In addition, the exhaust valve can be connected to a device to aid or supplement breathing by the patient, such as a ventilator.

A second aspect of the invention provides a method of delivering an aerosol to a patient, comprising providing an aerosol inhalation device; inserting a distal portion of said aerosol inhalation device into a breathing passage of the patient; and permitting the patient to inhale the aerosol. The inhalation device includes an aerosol source for generating an aerosol; a first conduit, having a proximal end, the first conduit providing passage of the aerosol to the patient; a first chamber at the proximal end of the first conduit, adjacent to the nebulizer; a second conduit providing passage of a gaseous medium exhaled from the patient; a second chamber; and a first valve disposed between the first chamber and the second chamber. The first valve remains closed during exhalation by the patient and opens at least partially during inhalation. The device also includes a second valve disposed between the second conduit and said second chamber, which remains closed during inhalation by the patient and opens at least partially during exhalation by the patient. The gaseous medium exhaled by the patient can optionally contain material from which the aerosol is formed, such as liquid droplets. The device can optionally include an exhaust port, adjacent to the second chamber, such as, for example, above the second chamber.

Another aspect of the invention provides a method of manufacturing an aerosol inhalation device. The method includes providing an aerosol source for generating an aerosol; connecting to the aerosol source a first conduit, the conduit having a proximal end, for providing passage of the aerosol; positioning a first chamber at the proximal end of the first conduit, adjacent to the aerosol source; connecting a second chamber to the first chamber by a first valve disposed between said first chamber and said second chamber; and connecting to the second chamber a second conduit by a second valve disposed between the second conduit and the second chamber. The method of manufacturing an aerosol inhalation device can further include the step of connecting an exhaust port to the second chamber. For example, the exhaust port can be above the second chamber. The aerosol source can comprise a nebulizer.

These and other aspects of the invention will be apparent to one skilled in the art in view of the ensuing disclosure and appended claims.

BRIEF DESCRIPTION OF THE DRAWINGS

The accompanying drawings illustrate preferred embodiments of the invention, as well as other information pertinent to the disclosure, in which.

DETAILED DESCRIPTION OF THE INVENTION

The present invention is directed to improved inhalation devices, and to methods for making and using the devices. The devices provide delivery of aerosols to patients.

While the term "aerosol" is commonly used to refer to a mist of liquid droplets, the term as used herein refers to a suspension of solid or liquid particles in a gas. Thus, it will be recognized by one skilled in the art that the term "aerosol" includes aerosols containing particles of liquid and/or powder, and encompasses forms such as smokes, fogs, and mists. In addition, the term "particles" is intended to encompass solid particles as well as particles or droplets of liquid.

The term "exhalate" as used herein refers to gases and other material emanating from an exhaling patient. The exhalate is alternately referred to herein as "gaseous medium" or "gaseous media" and can include some of the material in the aerosol that was not delivered to the patient's lungs, such as, for example, liquid droplets or solid particles.

The term "carrier gas" as used herein refers to a gas, such as air or oxygen, used to carry aerosol to a patient, and includes gas used in generating an aerosol.

Aerosols of any particles of respirable size containing medicaments or other substances suitable for delivery to the lungs of a patient can be used in the methods and devices of the present invention. As used herein the term "particles of respirable size" means particles that have an average diameter of less than about 10 microns, preferably less than about 8 microns, more preferably less than about 6 microns and still more preferably less than about 5 microns. Generally such particles have average diameters of about 0.2 microns or greater, typically about 0.3 microns or greater, and frequently about 0.4 microns or greater, and often about 0.5 microns or greater. For example, aerosol particles for delivery to a patient according to the methods and devices of the present invention will typically have average diameters from about 0.4 to about 2 microns. However, it will be recognized by those skilled in the art that an aerosol generally will also contain some fraction of particles that are larger than respirable size and/or larger agglomerates comprising several individual particles of respirable size.

The devices and methods of the invention provide improved delivery of diagnostic and therapeutic aerosols to patients. The devices and methods of the present invention reduce the amount of therapeutic or diagnostic material that is wasted by not being delivered to the patient. The improved operation of the devices of the invention also reduces the need for adjusting the flow of oxygen or air used to carry the aerosol to a patient, by providing a system of valves that can compensate for variations in the patient's breathing.

The present invention is further described with respect to the drawings. The drawings are exemplary in nature and are not to be construed as limiting the scope of the appended claims.

Figure 1:
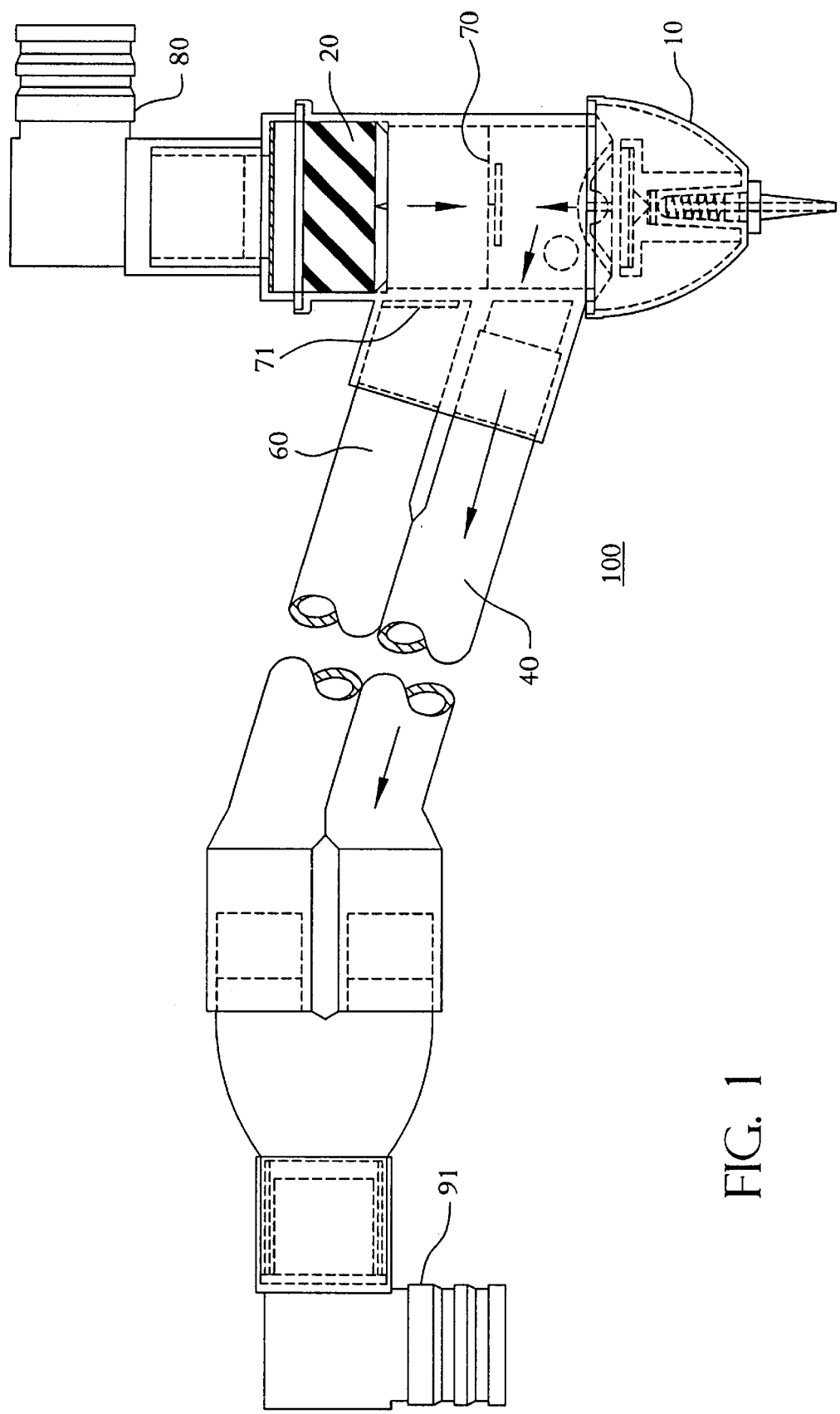
FIG. 1: is an isometric elevation view of a preferred aerosol inhalation device of this invention, illustrating some of the more important connections and features in phantom, and optional substance recovery media in cross-section, and illustrating the flow of aerosol during inhalation.
Figure 2:
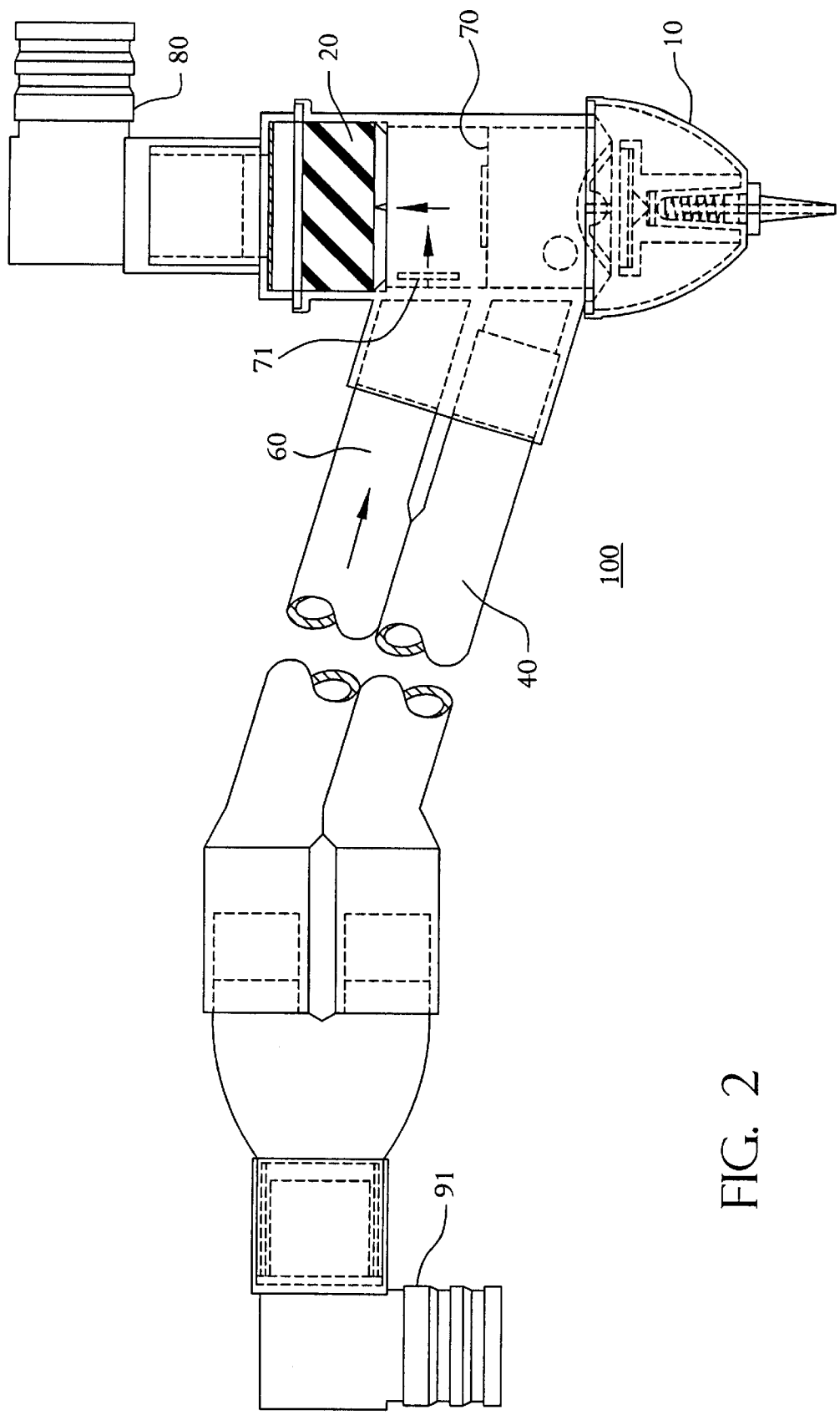
FIG. 2: is an isometric elevation view of a preferred aerosol inhalation device of this invention, illustrating some of the more important connections and features in phantom, and optional substance recovery media in cross-section, and illustrating the flow of exhalate during exhalation.

In FIGS. 1 and 2, there is shown a preferred aerosol inhalation device 100. This device 100 contains some basic elements which represent groups of constituent parts that are labeled together for convenience. These elements include a nebulizer 10 for producing an aerosol and an exhaust port 80. As a patient breathes through a mouthpiece (not shown) attached to the fitting 91 located at the distal end 90 of the device 100, aerosol mist and compressed air are received through first (intake) chamber 50, and valve 70 opens at least partially. As the patient exhales, exhalate is channeled through second (outlet) conduit 60 and valve 71, to second chamber 51 and exhaust port 80.

Valves are known for use in devices that deliver aerosols to patients. In known devices, such as the "Swirler®" device manufactured by Amici, Inc. of Spring City, Pa., valves are generally located within the conduit by which the aerosol is delivered to a patient (intake conduit) and/or within the conduit that removes exhaled gases and excess aerosol (outlet conduit). By obstructing the intake conduit, the valves can entrap material, e.g., large droplets or condensate, thus wasting expensive medicaments. The location of a valve within the outlet conduit, however, is generally not detrimental to the delivery of an aerosol to a patient. The location of a valve within the outlet conduit may be preferred because a valve located within the outlet conduit may collect unused aerosol, which can then return to the aerosol source.

In contrast, in the devices of the present invention, there is no valve directly obstructing the intake conduit 40 (i.e. no valve in the direct path between the aerosol inlet and the mouthpiece). Rather, a first valve 70 is disposed between two chambers 50 and 51, the two chambers being located at the proximal end of the intake conduit 40 and the outlet conduit 60 respectively. The outlet conduit 60 allows for passage of exhalate from the device, and can be connected to an exhaust port 80. The first valve 70 opens at least partially during inhalation by a patient, as shown in FIG. 1, allowing intake of air in response to inhalation, thus permitting the rate of flow of carrier gas remain constant rather than having to be adjusted in response to variations in the patient's breathing. During the opening of the first valve 70, aerosol particles, such as liquid droplets, that may have collected on the valve during exhalation can return to the aerosol source, such as a nebulizer, and can be recovered and used to generate additional aerosol. This recovery of material further reduces waste. During exhalation, the first valve 70 is closed, so that exhalate is routed through the second chamber 51.

A second valve 71 is disposed at the proximal end of the outlet conduit 60, and opens only during exhalation, as shown in FIG. 2, allowing for the release of exhaled gases and excess aerosol material that may have collected on the valve. Also shown is optional filtration device 20.

Figure 3:
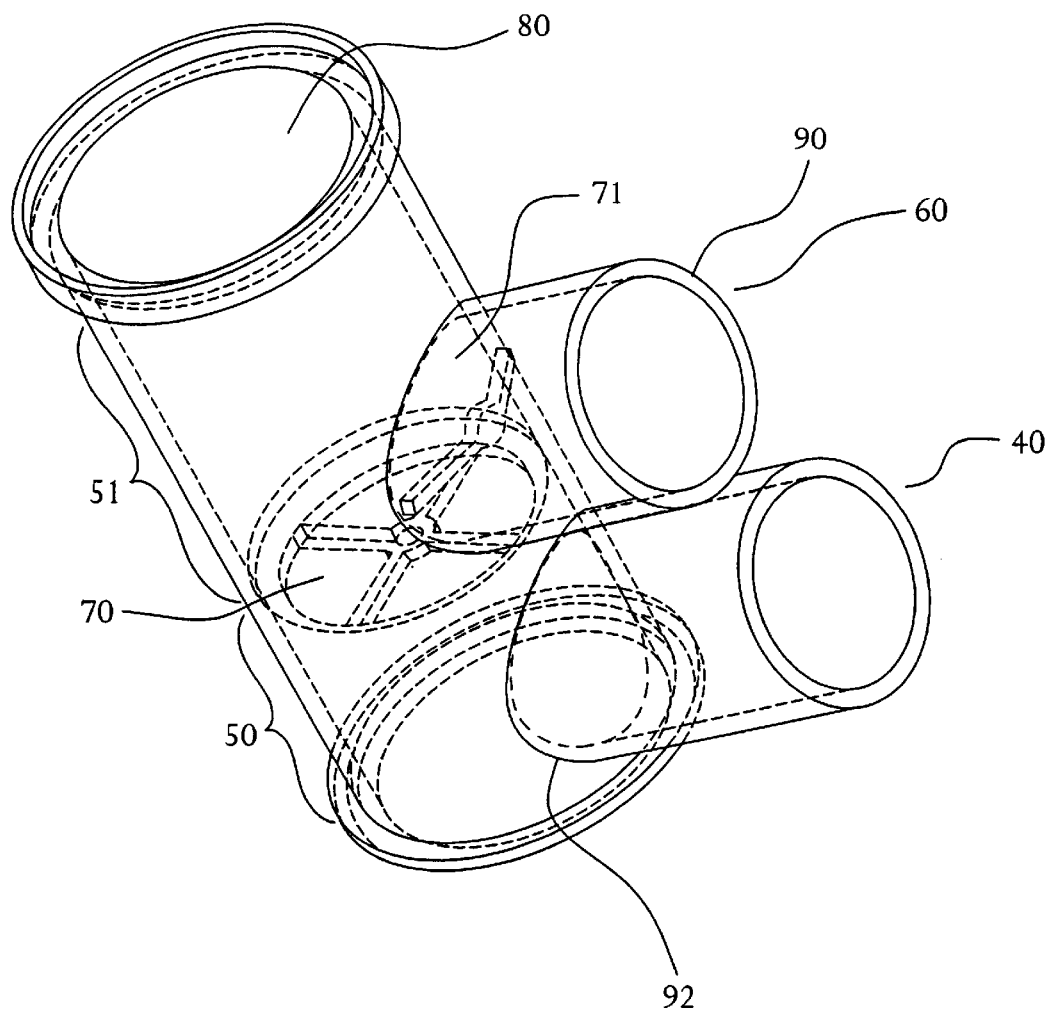
FIG. 3: is an isometric view of the portion of a preferred aerosol inhalation device of the invention that includes the novel valve configuration.

With reference to FIG. 3, aerosol enters the bottom of the device from an aerosol source (not shown). First chamber 50 is located at the proximal end 92 of first conduit 40. Valve 70 is disposed between first chamber 50 and a second chamber 51. As a patient breathes through a mouthpiece attached to a fitting (not shown) at the distal end 90 of the first conduit 40, first valve 70 opens at least partially and second valve 71 remains closed. Aerosol and gas are received through first (intake) conduit 40. As the patient exhales, exhaust gases are channeled through second (outlet) conduit 60 and valve 71, and valve 70 remains closed. Exhalate leaves the device through exhaust port 80.

In preferred embodiments, the inhalation devices of the invention also include preferred valves 70 and 71. In some inhalation devices, including the devices of the present invention, one-way valves are utilized to maximize inhalation of therapeutic or diagnostic aerosols and prevent exhalation of exhaust gases into the portion of the device where the aerosol is generated. Such valves are commonly made of flexible materials such as latex. However, many patients have allergies to latex, which can result in severe adverse reactions. Therefore, it is preferred that the valves of the invention not contain latex and even more preferably, the valves are made partially or entirely from a latex-free material such as, for example, polyvinyl chloride or silicone. The structure of the valves is not critical, and can be any structure or form of one-way valves well known to those skilled in the art.

The aerosol inhalation devices of the invention can also optionally include a filtration device to further reduce waste of therapeutic or diagnostic materials. Such filtration devices typically include a substance recovery medium to capture a portion of exhaled particles. Substance recovery media are optional and are described in U.S. Pat. No. 5,603,314, the disclosures of which are hereby incorporated herein by reference in their entirety.

In addition, the aerosol inhalation devices of the invention can include a rain-off chamber for returning a portion of exhaled particles to the aerosol source. Rain-off chambers are described in U.S. Pat. No. 5,611,332, the disclosures of which are hereby incorporated herein by reference in their entirety.

In preferred embodiments, the improved devices and methods of the invention can deliver at least about two times as much aerosol to a patient as comparable devices having valves disposed within the intake and/or outlet conduits. More preferably, the devices and methods of the present invention may deliver about three times as much, or more, aerosol as such known devices.

The methods and devices of the invention utilize an aerosol source. An exemplary aerosol source is a nebulizer. The nebulizers described hereinabove are used for generating aerosols from liquids. Devices for generating and delivering liquid medicaments in aerosol form are described in U.S. Pat. Nos. 5,603,314, 5,611,332, and 5,630,409, the disclosures of which are hereby incorporated herein by reference in their entirety. However, as noted above, aerosols can be made from liquid particles or solid particles. The aerosol source can be any aerosol source known to those skilled in the art, including pressurized and non-pressurized sources. Examples of suitable aerosol sources include any aerosol source that produces an aerosol involving turbulent fluid flow, such as, for example, a pressurized aerosol canister containing a propellant based medicinal aerosol formulation, or an aerosol canister in combination with an actuator through which the aerosol passes. Dry powder aerosol sources such as pump spray nebulizers, and the like, are also suitable for use in connection with the claimed invention. For example, powders can be placed in an aerosol container with a gas or liquid propellant, and if desired, with one or more pharmaceutically acceptable adjuvants such as humidifying agents or dispersing agents. In addition, nebulizers can be modified or manufactured for use with solid particles. Aerosols of solid particles can be delivered in the form of suspensions or dispersions, or as dry powders. Aerosols of solid particles, such as powders, and aerosol sources for use in generating aerosols of solid particles, are disclosed, for example, in U.S. Pat. Nos. 5,899,201; 5,887,586; and 5,894,964, the disclosures of which are hereby incorporated herein by reference in their entirety.

Although the invention is described above in terms of exemplary embodiments, it is not limited thereto. Rather, the invention is to be construed to cover other variations and embodiments which may be made by those skilled in the art without departing from the scope and range of equivalents of the appended claims.

What is claimed is:

1. An aerosol inhalation device for delivering an aerosol mist to a patient, comprising:
   an aerosol source for generating an aerosol;
   a first conduit for providing passage of said aerosol to a patient, said first conduit having a proximal end;
   a first chamber at the proximal end of said first conduit, said first chamber located adjacent to said aerosol source, said first chamber located between the first valve and the aerosol source;
   a second chamber that receives a gaseous medium exhaled from a patient;
   a first valve disposed between said first chamber and said second chamber, said first valve remaining closed during exhalation by a patient and opening at least partially during inhalation;
   a second conduit for providing passage of the gaseous medium exhaled from a patient to the second chamber; and
   a second valve disposed between said second conduit and said second chamber, said second valve remaining closed during inhalation by a patient and opening at least partially during exhalation by a patient.

2. The aerosol inhalation device of claim 1, further comprising an exhaust port located proximally from the second conduit.

3. The aerosol inhalation device of claim 2, further comprising a filtration device that captures a portion of said exhaled droplets while permitting a gas contained within said gaseous medium to pass through to said exhaust port.

4. The aerosol inhalation device of claim 1, wherein said second chamber is located at the proximal end of said second conduit.

5. The aerosol inhalation device of claim 1, wherein said valve is a diaphragm valve.

6. The aerosol inhalation device of claim 1, wherein at least one of said valves is latex-free.

7. The aerosol inhalation device of claim 1, wherein at least one of said valves comprises polyvinyl chloride or silicone.

8. The aerosol inhalation device of claim 1, wherein at least one of said valves comprises silicone.

9. The aerosol inhalation device of claim 1, wherein said second valve is located at the proximal end of said second conduit.

10. The aerosol inhalation device of claim 1, wherein said aerosol source comprises a nebulizer.

11. The aerosol inhalation device of claim 10, wherein the gaseous medium exhaled by said patient comprises liquid droplets.

12. The aerosol inhalation device of claim 1, wherein the aerosol comprises liquid droplets.

13. The aerosol inhalation device of claim 1, wherein the aerosol comprises solid particles.

14. The device of claim 1, wherein the aerosol source and the first chamber are not separated by any valve.

15. The device of claim 1, wherein the first conduit and the first chamber are not separated by any valve.

16. The device of claim 1, wherein the first chamber and second chamber are included within a single cylindrical tube.

17. The device of claim 1, wherein the first valve prevents flow of a gaseous medium from the second chamber to the first chamber.

18. A method of providing an aerosol mist to a patient, comprising a) providing an aerosol inhalation device which includes: an aerosol source for generating an aerosol;

a first conduit for providing passage of said aerosol to a patient, said first conduit having a proximal end;

a first chamber at the proximal end of said first conduit, said first chamber located adjacent to said aerosol source, said first chamber located between the first valve and the aerosol source;

a second chamber that receives a gaseous medium exhaled from a patient;

a second conduit for providing passage of a gaseous medium exhaled from a patient to the second chamber;

a first valve disposed between said first chamber and said second chamber, said first valve remaining closed during exhalation by a patient and opening at least partially during inhalation; and a second valve disposed between said second conduit and said second chamber, said second valve remaining closed during inhalation by a patient and opening at least partially during exhalation by a patient.

b) inserting a distal portion of said aerosol inhalation device into a breathing passage of a patient; and c) permitting a patient to inhale said aerosol.

19. The method of claim 18, wherein said aerosol comprises liquid droplets.

20. The method of claim 18, wherein said gaseous medium exhaled from said patient comprises liquid droplets.

21. The method of claim 20, further comprising recycling a portion of said exhaled droplets back to said aerosol source, forming an aerosol from said recycled droplets, and delivering said recycled droplets back to a patient.

22. The method of claim 18, wherein said aerosol comprises solid particles.

23. The method of claim 18, wherein said aerosol source comprises a nebulizer.

24. The method of claim 18, wherein said valve comprises silicone.

25. A method of manufacturing an aerosol inhalation device, comprising:

providing an aerosol source for generating an aerosol;

connecting to said aerosol source a first conduit, said first conduit having a proximal end;

positioning a first chamber at the proximal end of said first conduit, so that the first chamber is adjacent to said aerosol source;

connecting a second chamber to said first chamber by a first valve disposed between said first chamber and said second chamber, such that the first chamber is between the aerosol source and the first valve; and connecting to the second chamber a second conduit by a second valve disposed between said second conduit and said second chamber.

26. The method of claim 25, further comprising the step of forming the first and second valves from silicone.

27. The method of claim 25, further comprising connecting an exhaust port to said second chamber.

* * * * *